(12) United States Patent
Ng et al.

(10) Patent No.: US 10,209,188 B2
(45) Date of Patent: Feb. 19, 2019

(54) METHODS AND SYSTEMS FOR INCORPORATING BIO-SENSORS IN DRONES TO WIRELESSLY DETECT BIOLOGICAL MOLECULES AND HAZARDS

(71) Applicant: The United States of America as represented by the Secretary of the Navy, Washington, DC (US)

(72) Inventors: Kin Chiu Ng, Fresno, CA (US); Subrata Sanyal, Eastvale, CA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 15/801,296

(22) Filed: Nov. 1, 2017

(65) Prior Publication Data

US 2018/0120227 A1 May 3, 2018

Related U.S. Application Data

(60) Provisional application No. 62/416,267, filed on Nov. 2, 2016.

(51) Int. Cl.
*G01J 3/30* (2006.01)
*G01N 21/63* (2006.01)
*B64C 39/02* (2006.01)
*G08G 5/00* (2006.01)
*G01D 21/02* (2006.01)
*G01N 21/64* (2006.01)

(52) U.S. Cl.
CPC ......... *G01N 21/636* (2013.01); *B64C 39/024* (2013.01); *G01D 21/02* (2013.01); *G01N 21/645* (2013.01); *G01N 21/6454* (2013.01); *G08G 5/0013* (2013.01); *G08G 5/0056* (2013.01); *G08G 5/0069* (2013.01); *G08G 5/0073* (2013.01); *G08G 5/0086* (2013.01); *B64C 2201/027* (2013.01); *B64C 2201/126* (2013.01); *G01N 2021/637* (2013.01); *G01N 2021/6415* (2013.01); *G01N 2021/6421* (2013.01); *G01N 2021/6491* (2013.01); *G01N 2201/0214* (2013.01)

(58) Field of Classification Search
CPC ........ G01J 3/02; G01J 3/4406; G01N 21/718; G01N 21/645; G01N 21/6458
USPC ........................................................ 356/318
See application file for complete search history.

(56) References Cited

U.S. PATENT DOCUMENTS

| | | | |
|---|---|---|---|
| 2003/0085348 A1* | 5/2003 | Megerle | G01N 1/2202 250/287 |
| 2017/0003684 A1* | 1/2017 | Knudsen | G01N 21/51 |

* cited by examiner

*Primary Examiner* — Md M Rahman
(74) *Attorney, Agent, or Firm* — Christopher A. Monsey

(57) ABSTRACT

Exemplary methods and systems for incorporating bio-sensors in drones to wirelessly detect biological molecules and hazards without exposing an operator to harmful contaminants or conditions. Bio-sensors can incorporate simultaneous dual-detection methods to ensure accuracy of measurements. Methods of operation include registering blank and safe air profiles for comparison against unknown air profiles to accurately determine the presence of bio-contaminants in unknown air.

**9

Figure 1:
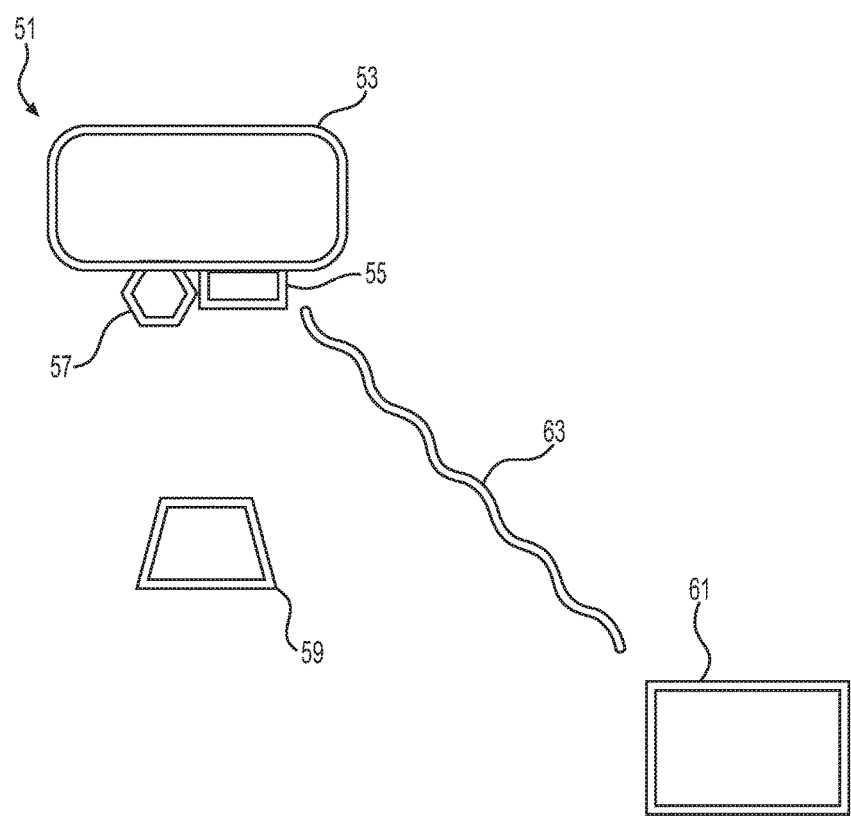
Figure 2:
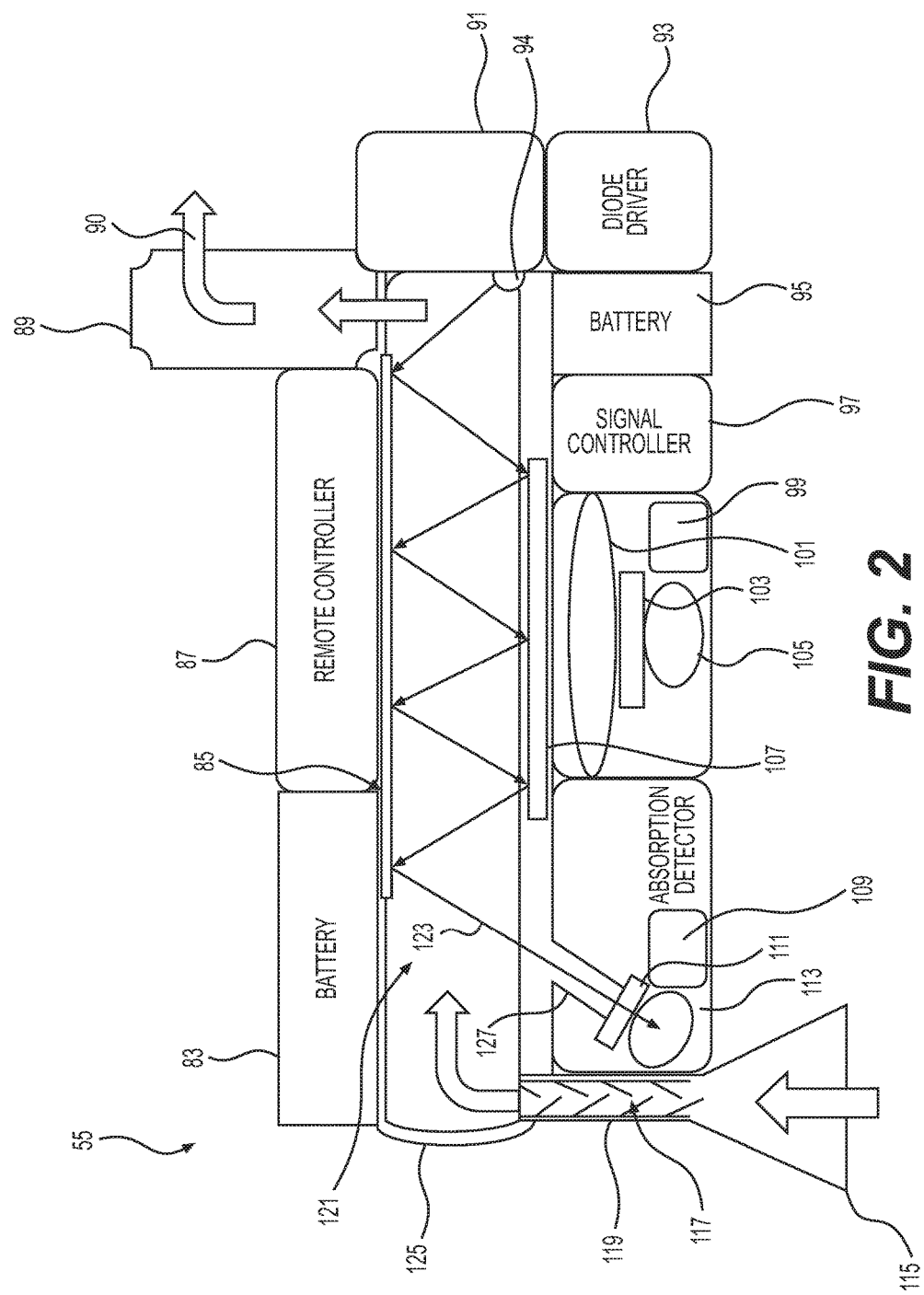

METHODS AND SYSTEMS FOR INCORPORATING BIO-SENSORS IN DRONES TO WIRELESSLY DETECT BIOLOGICAL MOLECULES AND HAZARDS

CROSS-REFERENCE TO RELATED APPLICATIONS

The present application claims priority to U.S. Provisional Patent Application Ser. No. 62/416,267, filed Nov. 2, 2016, entitled "Biosensor for Drone Applications," the disclosure of which is expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (Navy Case 200,385) is assigned to the United States Government and is available for licensing for commercial purposes. Licensing and technical inquiries may be directed to the Technology Transfer Office, Naval Surface Warfare Center (NSWC) Corona Division, e-mail: CRNA_CTO@navy.mil.

BACKGROUND AND SUMMARY OF THE INVENTION

The present invention relates generally to a drone-sensor system capable of wirelessly detecting the presence of hazardous agents without requiring people (e.g. emergency responders) from being endangered by those hazardous agents. The present invention can detect, monitor, and analyze passive and active threats and hazards at incident scenes in real time to rapidly identify hazardous agents and contaminants. Using a drone-sensor system can protect against multiple hazards by preventing unnecessary exposure to such hazards while also remotely scanning for signs of life and decomposition to identify and locate casualties and fatalities to assist in evacuation near an accident or contamination scene.

According to an illustrative embodiment of the present disclosure, a drone-sensor system can be attached to an unmanned aerial vehicle (UAV). A system controller in the drone-sensor system can transmit preprogrammed instructions to flight control systems to direct the drone-sensor system towards a condition or object of interest. A remote controller can allow an operator to manually control the drone-sensor system or send new instructions to the drone-sensor system. A plurality of sensors can allow the drone-sensor system to identify potential threats or conditions of interest so that the drone-sensor system can approach the threat or condition and use an onboard bio-sensor to detect the presence of a biological agent.

According to a further illustrative embodiment of the present disclosure, a fluorescence-detector for sensing laser-excited-molecular-fluorescence and an absorption-detector for sensing laser-intensity can be used as simultaneous methods of detecting the presence of biomolecules in an air sample.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 1 shows an overview of an exemplary drone-sensor system in an operational environment.

FIG. 2 shows an exemplary bio-sensor.

FIG. 3 shows an exemplary bio-sensor with an exemplary housing structure.

FIG. 4 is a block diagram illustrating interactions between various components of an exemplary drone-sensor system.

FIG. 5 shows an exemplary method for operating a drone-sensor system.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

FIG. 1 shows an exemplary drone-sensor system 51 in an exemplary operating environment. A drone-sensor system 51 can include a drone 53, a bio-sensor 55, and a video-camera system 57. A drone-sensor system 51 can be remotely operated using a remote control station 61 through wirelessly transmitted control signals 63. A video-camera system 57 or other sensors (e.g., the Global Positioning System (GPS), infrared sensor, etc.) can be used to gather information about the operating environment, such as location of the drone-sensor system 51 or a condition of interest 59 (e.g., a chemical spill). A drone-sensor system 51 can be positioned near a condition of interest 59 so that a bio-sensor 55 can determine the presence of particular chemical or bio-agents in proximity to the condition of interest 59.

FIG. 2 shows an exemplary bio-sensor 55 which can be used in a drone-sensor system. Biomolecules can enter the bio-sensor 55 through a first air inlet 115 (e.g., an inverted funnel) and stem 119 (e.g., a tube 3" long and 0.25" inner diameter). Baffles 117 in spiral stages prevent scattered light or droplets of water from entering the bio-sensor 55. First air inlet 115 and stem 119 can have a grooved surface for facilitating drainage of liquids captured by baffles 117. Sampling chamber 121 can be a quartz rectangular pipe or cell (e.g., a 0.5" by 0.5" by 4" box, or a pipe with about a 20 mL volume) with apertures on opposite ends to allow air to enter and exit. Part of sampling chamber 121 is coated with a reflective coating 85 (e.g., aluminum with $MgF_2$ overcoat) to reflect both a laser beam 123 and fluorescence emissions. A non-reflective black holder 125 surrounds sampling chamber 121 to help keep the humidity-level in the sampling chamber 121 the same as that of the external atmosphere for preventing possible condensation in the chamber. Pump 89 can draw air through the bio-sensor 55 at a fixed rate for consistent testing results. The air passes through sample chamber 121, enters pump 89, and exits through a first air outlet 90.

Biomolecules can absorb laser wavelengths of about 275 nm, resulting in a signature absorption signal. Biomolecules selectively absorb laser radiation, get excited, and generate a signature fluorescence signal of about a 345 nm wavelength. Reading a signature absorption signal and signature fluorescence signal in tandem can increase the confidence for positive detection. To detect both signals, an exemplary bio-sensor 55 can include a fluorescence detector 105 (e.g. a high quantum efficiency avalanche photodiode or array of photodiodes) for sensing laser-excited-molecular-fluorescence, and an absorption-detector 113 (e.g. a silicon photo-diode) for sensing laser-intensity. Therefore, a higher fluorescence-signal represents more biomolecules; a lower absorption-signal also represents more biomolecules because more of the laser-beam is absorbed. Directional laser beam 123 is produced by a laser diode 91 (e.g. a 1-100 mW radiation power diode emitting radiation of 275 nm wavelength) which uses a diode driver 93 (e.g., a 50-200 mA current power source). A first quartz lens 94 collimates and directs the laser beam 123 into the sampling chamber 121. The laser beam 123 is reflected within the sampling chamber 121 by reflective coating 85 and reflective filter 107 (e.g. a 345 mu band pass filter reflective to 275 nm lasers). A second quartz lens 101 collects the ~345 nm wavelength of fluorescent-light (that is emitted by biomolecules that could be present in the contaminated air drawn in to the sampling chamber 121, and passed through the reflective filter 107), and focuses the fluorescent light through a first spectral filter 103 that allows very-narrow band of the ~345 nm wavelength of light to go through and onto the fluorescence detector 105. The laser beam 123 enters a small-channel 127 that has a small inner diameter (e.g., ~2 mm) and designed to be aligned at about 45° to the vertical-axis, preventing the detector receiving light from first air inlet 115. A second spectral filter 111 allows only ~275 nm radiation-wavelength to pass through to the absorption-detector 113. Direct air-sampling requires highly-sensitive detection because the amount of biomolecules in air is expected to be very low. The laser beam 123 enters the sampling chamber 121 at an angle. The optical path of laser beam 123 is lengthened in the sampling chamber 121 by laser-reflection from the reflective coating 85 and the reflective filter 107 to maximize the amount of air impacted by the laser beam 123. A longer optical path increases the number of biomolecules in the drawn air exposed to the laser beam 123 for absorption and excitation, thereby allowing for stronger and more reliable signal generation.

A remote-controller 87 can interface with a signal-controller 97 for data-processing, analog to digital (A/D) conversion, noise-filtering and for signal-average, with a system controller within the drone-sensor system for GPS speed, direction, geographical coordinates, photographing, and video-taking; and with a server at a remote control station where date and time are registered, raw-data can be encoded, decoded, and kept in database; and the data are presented in user-defined formats with conventional software. Power to a bio-sensor 55 can be provided by the drone-sensor system's power supply, or a battery 83 can provide an independent power source. Power to a fluorescence detector 105 can be provided by a first power supply 99, and power to an absorption-detector 113 can be provided by a second power supply 109. All the components in bio-sensor 55 are mounted securely, and electronic circuitry is assembled on printed boards.

Figure 3:
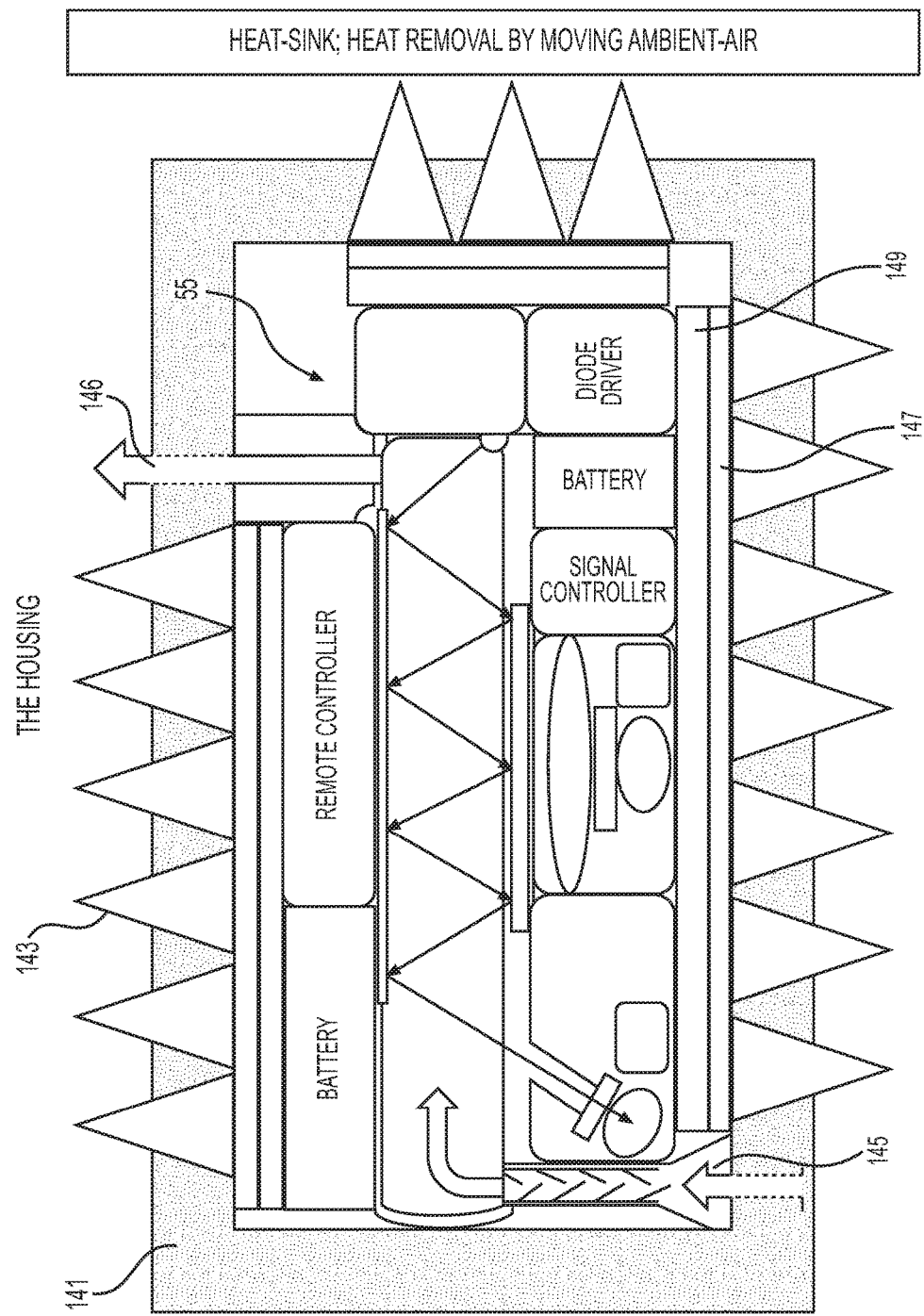

FIG. 3 shows an exemplary bio-sensor 55 with a housing structure. Bio-sensor can be enclosed in a sealed, robust housing container 141 with protection/insulation from ambient-light, precipitation, vibration, and electro-magnetic or other forms of radiation including heat. First and second thermal-electric cooling elements/modules sections 147 and 149, respectively can be used for cooling the electronic components by conductively absorbing heat from the components so they continue to function properly and generate meaningful signals. A plurality of heat sinks 143 allow heat to be removed from the first thermal-electric cooling elements/modules 147 by convective heat transfer to ambient air as the drone-sensor system moves. A second air inlet 145 can allow air to pass through the housing container 141 to enter a first air inlet. A second air outlet 146 in housing container 141 can connect to a first air outlet of a pump to allow air to leave the bio-sensor 55.

Figure 4:
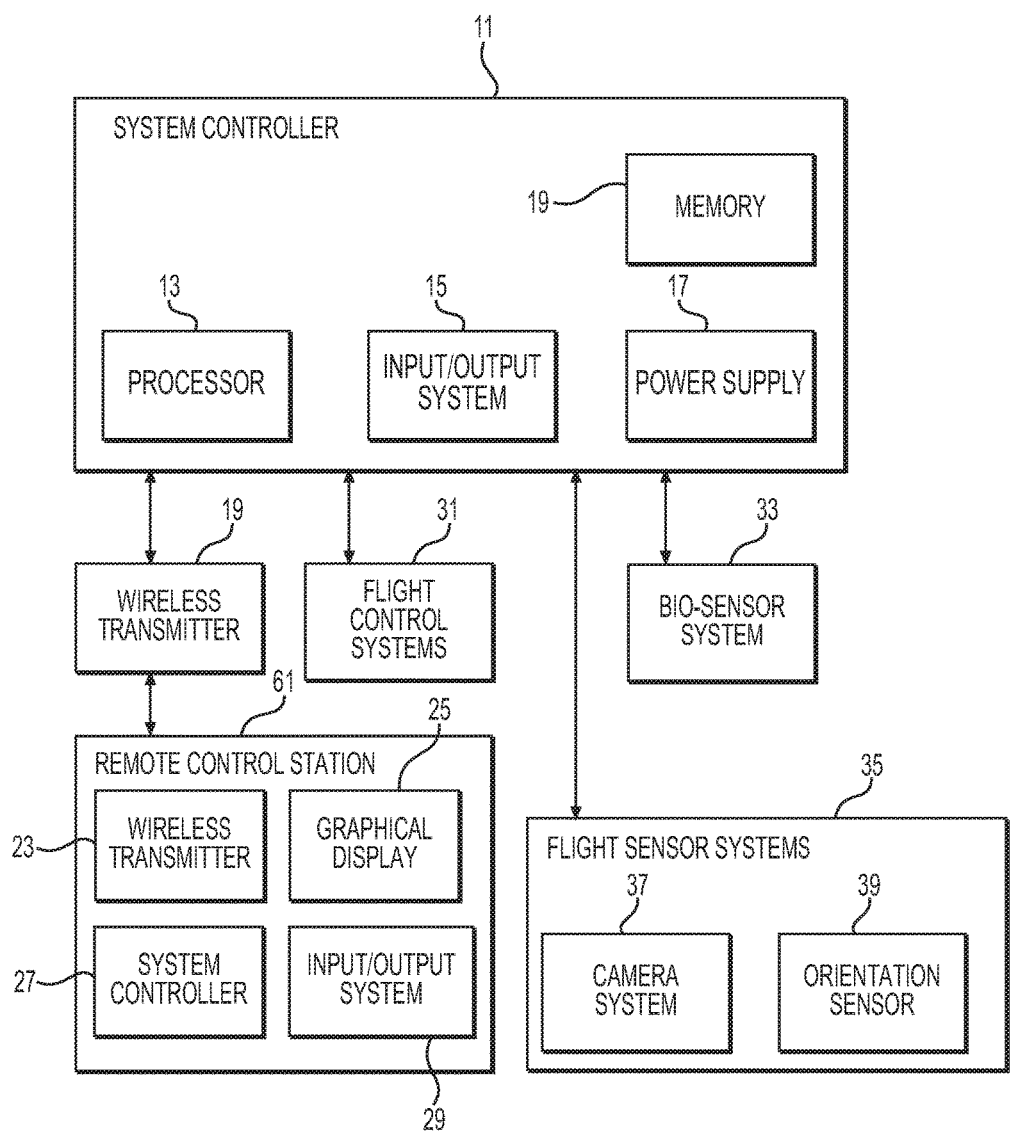

FIG. 4 shows a block diagram of the component interactions between systems and subsystems of an exemplary drone-sensor system. A first system controller 11 includes a processor 13, first input/output (I/O) system 15, power supply 17, and memory 19. The first system controller 11 interacts with other system components, performs calculations, and allows for interaction with external systems through a first I/O system 15 (e.g., wired or wireless connections). Computer readable instructions stored in memory 19 can be passed to the processor 13 to carry out actions or tasks. First I/O system 15 can be used to add, update, or remove computer readable instruction stored in memory 19. First system controller 11 can be connected to a first wireless transmitter 19. A remote control station 61 can allow an operator or computer program to wirelessly transmit operational instructions to a first system controller 11. A first wireless transmitter 19 can communicate with a second wireless transmitter 23 within a remote control station 61. A remote controller 21 can include a second wireless transmitter 23, a graphical display 25, a second system controller 27, and a second I/O system 29. First system controller 11 can be connected to flight control systems 31, which control mechanical components for a drone's flight and movement. First controller 11 can be connected to bio-sensor system 33 (e.g., a bio-sensor and coupling cables) such that a plurality of signals can be sent to the first system controller 11 when bio-sensor system 33 detects a biological agent or hazard. First controller 11 can be connected to flight sensor systems 35, which can include a camera system 37 that can detect and identify environmental objects (e.g. a barrel with a particular label) or conditions (e.g. a fire). In an exemplary usage, camera system 37 can detect an obstacle and transmit the location of the obstacle to the first system controller 11, which can transmit a plurality of instructions to flight control system 31 so that flight control systems 31 can adjust the flight path of the drone-sensor system to avoid the obstacle. Flight sensor system 35 can also include other sensors, such as an orientation sensor 39 for determining the direction and tilt of the drone-sensor system. Additional embodiments can include an onboard GPS system for tracking a drone-sensor system or for guiding a drone-sensor system towards a particular location.

Figure 5:
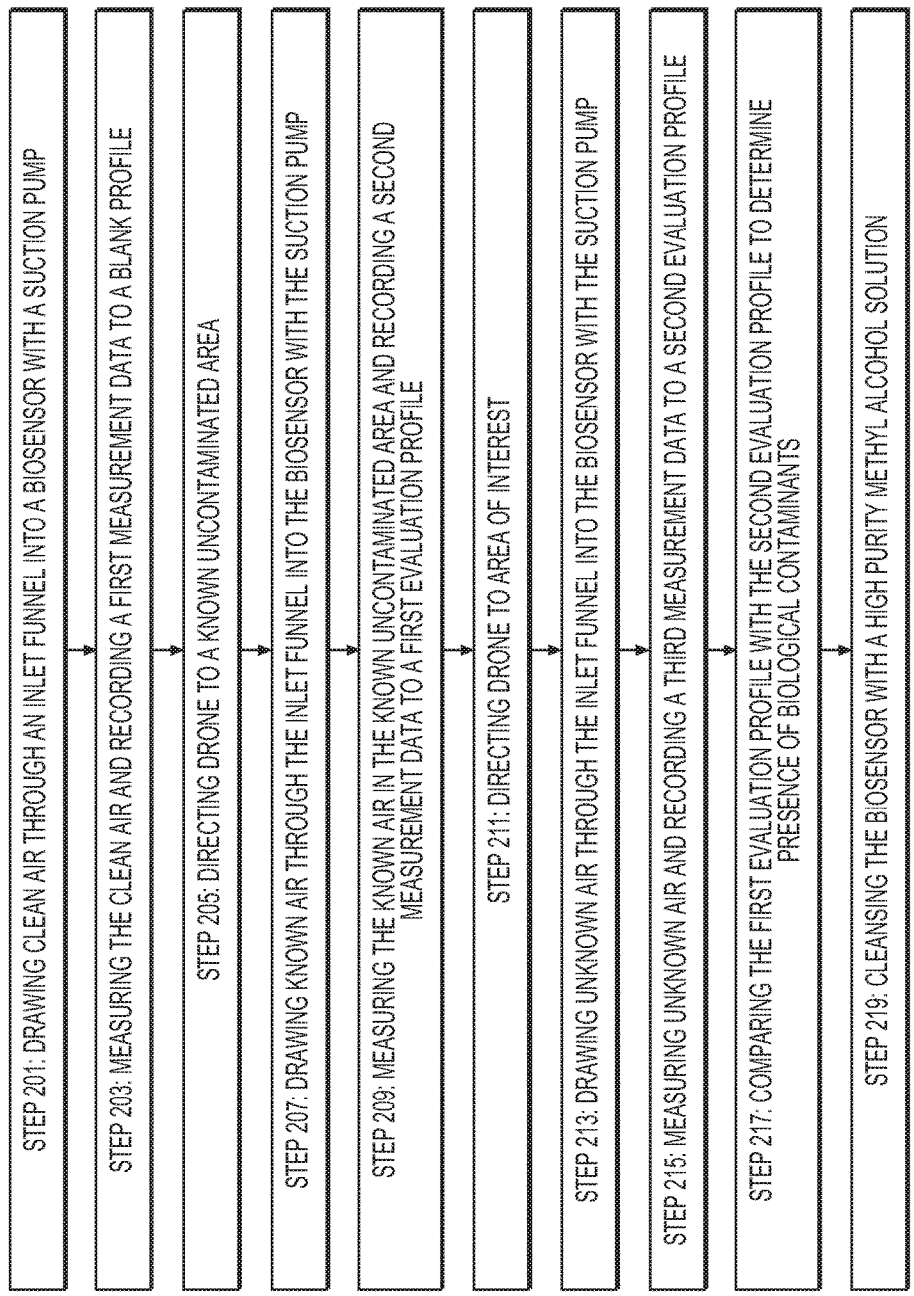

FIG. 5 shows an exemplary method of operating a drone-sensor system. At step 201, drawing clean air through an air inlet into a bio-sensor with a suction pump. At step 203, measuring the clean air and recording a first measurement data to a blank profile. At step 205, directing drone to a known uncontaminated area. At step 207, drawing known air through the air inlet into the bio-sensor with the suction pump. At step 209, measuring the known air in the known uncontaminated area and recording a second measurement data to a first evaluation profile. At step 211, directing drone to area of interest. At step 213, drawing unknown air through the air inlet into the bio-sensor with the suction pump. At step 215, measuring unknown air and recording a third measurement data to a second evaluation profile. At step 217, comparing the first evaluation profile with the second evaluation profile to determine presence of biological contaminant. At step 219, cleansing the bio-sensor with a high purity methyl alcohol solution.

Although the invention has been described in detail with reference to certain preferred embodiments, variations and modifications exist within the spirit and scope of the invention as described and defined in the following claims.

The invention claimed is:
1. A drone-sensor system comprising:
an unmanned aerial vehicle (UAV) comprising:
   a system controller comprising a processor, an input/output (I/O) system, memory, and a first power supply;
   a wireless transmitter electronically coupled to the system controller, wherein the wireless transmitter is configured to receive a plurality of instructions from a remote control station and transfer the plurality of instruction to flight control systems, flight sensor systems, and a bio-sensor;
   the flight control systems electronically coupled to the system controller, wherein the flight control systems maneuver the UAV based on instructions received from; and
   flight sensor systems comprising a video-camera system and an orientation sensor, wherein the flight sensor systems are electronically coupled to the system controller;
a bio-sensor comprising:
   a sampling chamber comprising a cell forming a first cavity section, a first and second aperture on a first and second end, respectively, a third and fourth aperture, a reflective filter, and a reflective coating;
   a laser diode configured to generate and direct a laser beam at a first wavelength through the third aperture into the sampling chamber and through the fourth aperture out of the sampling chamber, wherein the reflective filter is reflective to the first wavelength, wherein as a first optical path of the laser beam passes through the sampling chamber, the first optical path reflects off of the reflective coating and reflective filter at least once each;
   a first spectral filter;
   a fluorescence detector configured to detect a second wavelength and generate a first plurality of detection signals;
   a second spectral filter that allows the first wavelength to pass through;
   an absorption detector configured to detect the first wavelength and generate a second plurality of detection signals;
   a signal controller configured to receive the plurality of instructions from the system controller and transmit the first and second pluralities of detection signals to the system controller; and
   a pump, wherein the pump draws air into the sampling chamber through the first aperture and draws air out of the sampling chamber through the second aperture;
   wherein when the laser beam hits biomolecules in the sampling chamber, the wavelength of the laser beam changes to the second wavelength; wherein the reflective filter and the first spectral filter allow the second wavelength to pass through to the fluorescence detector;
   wherein when the laser beam is not absorbed by biomolecules in the sampling chamber, the laser beam passes through the second spectral filter to the absorption detector; and
   a housing structure comprising:
      an exterior and interior wall;
      a plurality of heat sinks; and
      at least one thermal-electric cooling module;
      wherein the interior wall forms a second cavity section, wherein the bio-sensor is within the second cavity section, wherein the bio-sensor is mechanically coupled to the housing structure, wherein each of the at least one thermal-electric cooling modules is in contact with the bio-sensor, wherein the plurality of heat sinks are in contact with the at least one thermal-electric cooling module, wherein heat generated by the bio-sensor is transferred to the plurality of heat sinks through the at least one thermal-electric cooling module, wherein heat in the plurality of heat sinks is dissipated to surrounding air through convective heat transfer, wherein the housing structure is mechanically coupled to the UAV.

2. The system of claim 1, wherein the bio-sensor is electrically coupled to the UAV such that the first power supply powers the bio-sensor.

3. The system of claim 1, wherein the laser diode, the fluorescence detector, the absorption detector, and the pump are powered by a second, a third, a fourth, and a fifth power supply, respectively.

4. The system of claim 1, wherein the bio-sensor further comprises:
an air inlet funnel comprising a funnel section and a tube section, further comprising plurality of baffle on an interior surface of the tube section.

5. The system of claim 1, wherein the flight sensor systems further comprise a GPS system comprising a GPS receiver.

6. A method of detecting bio-molecules comprising:
providing an unmanned aerial vehicle comprising a bio-sensor;
drawing clean air through an air inlet into the bio-sensor with a suction pump;
measuring the clean air and recording a first plurality of measurement data to a blank profile;
directing the UAV to a known uncontaminated area;
drawing known air through the air inlet into a bio-sensor with the suction pump;
measuring the known air in the known uncontaminated area and recording a second plurality of measurement data to a first evaluation profile;
directing the UAV to area of interest;
drawing unknown air through the air inlet into a bio-sensor with the suction pump;
measuring unknown air and recording a third plurality of measurement data to a second evaluation profile; and
comparing the first evaluation profile with the second evaluation profile to determine presence of biological contaminants.

7. The method of claim 6, further comprising:
cleansing the bio-sensor with a high purity methyl alcohol solution after recording the third plurality of measurement data;
removing and replacing the suction pump with a new pump after recording the third plurality of measurement data.

8. A method of detecting bio-molecules comprising:
providing a drone-sensor system comprising:
   an unmanned aerial vehicle (UAV) comprising:
      a system controller comprising a processor, an input/output (I/O) system, memory, and a first power supply a wireless transmitter electronically coupled to the system controller, wherein the wireless transmitter is configured to receive a plurality of instructions from a remote control station and transfer the plurality of instruction to flight control systems, flight sensor systems, and a bio-sensor;

the flight control systems electronically coupled to the system controller, wherein the flight control systems maneuver the UAV based on instructions received from; and flight sensor systems comprising a video-camera system and an orientation sensor, wherein the flight sensor systems are electronically coupled to the system controller;

a bio-sensor comprising:

a sampling chamber comprising a cell forming a first cavity section, a first and second aperture on a first and second end, respectively, a third and four aperture, a reflective filter, and a reflective coating;

a laser diode configured to generate and direct a laser beam at a first wavelength through the third aperture into the sampling chamber and through the fourth aperture out of the sampling chamber, wherein the reflective filter is reflective to the first wavelength, wherein as a first optical path of the laser beam passes through the sampling chamber, the first optical path reflects off of the reflective coating and reflective filter at least once each;

a first spectral filter;

a fluorescence detector configured to detect a second wavelength and generate a first plurality of detection signals;

a second spectral filter that allows the first wavelength to pass through;

an absorption detector configured to detect the first wavelength and generate a second plurality of detection signals;

a signal controller configured to receive the plurality of instructions from the system controller and transmit the first and second pluralities of detection signals to the system controller; and a pump, wherein the pump draws air into the sampling chamber through the first aperture and draws air out of the sampling chamber through the second aperture;

wherein when the laser beam hits biomolecules in the sampling chamber, the wavelength of the laser beam changes to the second wavelength; wherein the reflective filter and the first spectral filter allow the second wavelength to pass through to the fluorescence detector;

wherein when the laser beam is not absorbed by biomolecules in the sampling chamber, the laser beam passes through the second spectral filter to the absorption detector; and a housing structure comprising:

an exterior and interior wall;

a plurality of heat sinks; and at least one thermal-electric cooling module;

wherein the interior wall forms a second cavity section, wherein the bio-sensor is within the second cavity section, wherein the bio-sensor is mechanically coupled to the housing structure, wherein each of the at least one thermal-electric cooling modules is in contact with the bio-sensor, wherein the plurality of heat sinks are in contact with the at least one thermal-electric cooling module, wherein heat generated by the bio-sensor is transferred to the plurality of heat sinks through the at least one thermal-electric cooling module, wherein heat in the plurality of heat sinks is dissipated to surrounding air through convective heat transfer, wherein the housing structure is mechanically coupled to the UAV;

drawing clean air through an air inlet funnel into the sampling chamber with the pump;

measuring the clean air and recording a first plurality of measurement data to a blank profile;

directing the UAV to a known uncontaminated area;

drawing known uncontaminated air through the air inlet funnel into the sampling chamber with the pump;

measuring the known uncontaminated air in the known uncontaminated area and recording a second plurality of measurement data to a first evaluation profile;

directing the UAV to an area of interest;

drawing unknown air through the air inlet funnel into the sampling chamber with the pump;

measuring unknown air and recording a third plurality of measurement data to a second evaluation profile; and comparing the first evaluation profile with the second evaluation profile to determine presence of biological contaminants.

9. The method of claim 8, further comprising:

cleansing the sampling chamber with a high purity methyl alcohol solution after recording the third plurality of measurement data;

removing and replacing the pump with a new pump after recording the third plurality of measurement data.

* * * * *